US010245213B2

(12) United States Patent
Wattellier et al.

(10) Patent No.: US 10,245,213 B2
(45) Date of Patent: Apr. 2, 2019

(54) DEVICE FOR RECONSTITUTING A PHARMACEUTICAL COMPOSITION (71) Applicant: EVEON, Montbonnot-Saint-Martin (FR)

(72) Inventors: Arnaud Wattellier, Laval (FR); Xavier Payet-Burin, Villard Bonnot (FR)

(73) Assignee: EVEON (FR)

( * ) Notice: Subject to any disclaimer, the term of this patent is extended or adjusted under 35 U.S.C. 154(b) by 193 days.

(21) Appl. No.: 15/330,061

(22) PCT Filed: Jan. 23, 2015

(86) PCT No.: PCT/EP2015/051311
§ 371 (c)(1),
(2) Date: Jul. 29, 2016

(87) PCT Pub. No.: WO2015/113897
PCT Pub. Date: Aug. 6, 2015

(65) Prior Publication Data
US 2017/0135903 A1 May 18, 2017

(30) Foreign Application Priority Data
Jan. 29, 2014 (EP) .................................... 14290010

(51) Int. Cl.
*A61J 1/20* (2006.01)
*A61J 1/14* (2006.01)
(Continued)

(52) U.S. Cl.
CPC ........... *A61J 1/2093* (2013.01); *A61J 1/1406* (2013.01); *A61J 1/20* (2013.01); *A61J 1/201* (2015.05);
(Continued)

(58) Field of Classification Search
CPC ................................. A61J 1/20; A61J 1/2089
See application file for complete search history.

(56) References Cited

U.S. PATENT DOCUMENTS 3,935,883 A * 2/1976 Stach .................. A61M 5/1782
141/27
7,220,245 B2 * 5/2007 Kriesel ............. A61M 5/14244
604/134

FOREIGN PATENT DOCUMENTS

DE 4408498 A1 5/1995
EP 2172182 A2 4/2010
(Continued)

OTHER PUBLICATIONS

International Search Report for Application No. PCT/EP2015/051311 dated Mar. 25, 2015.

*Primary Examiner* — Tony G Soohoo
*Assistant Examiner* — Elizabeth Insler
(74) *Attorney, Agent, or Firm* — Lerner, David, Littenberg, Krumholz & Mentlik, LLP (57) ABSTRACT A device for reconstituting a pharmaceutical composition from at least a first component in a first container and a second component in a second container. The device includes a fluidic unit having a first connector coupled to the first container, a second connector coupled to the second container, a pump, and a fluidic circuit connecting the first connector, the second connector and the pump. The first connector includes a crankpin in rotating engagement within a body and including an axial port fluidically couplable to the first container, a radial port fluidically connected to the axial port of the first connector, and at least one channel arranged therein so as to cooperate with the radial ports of the body of the first connector to selectively connect the (Continued)

axial port of the first connector with at least one channel portion of the fluidic circuit depending on the angular position of the crankpin.

15 Claims, 9 Drawing Sheets

(51) Int. Cl.
    *A61M 5/142*     (2006.01)
    *B65B 31/02*     (2006.01)

(52) U.S. Cl.
    CPC ............ *A61J 1/2048* (2015.05); *A61J 1/2068* (2015.05); *A61J 1/2086* (2015.05); *A61J 1/2096* (2013.01); *A61M 5/142* (2013.01); *B65B 31/02* (2013.01); *A61J 1/2017* (2015.05)

(56) References Cited

FOREIGN PATENT DOCUMENTS

| | | | |
|---|---|---|---|
| EP | 2258333 | A1 | 12/2010 |
| WO | 9513785 | A1 | 5/1995 |

\* cited by examiner

DEVICE FOR RECONSTITUTING A PHARMACEUTICAL COMPOSITION

CROSS REFERENCE TO RELATED APPLICATIONS

The present application is a national phase entry under 35 U.S.C. § 371 of International Application No. PCT/EP2015/051311 filed Jan. 23, 2015, published in English, which claims priority from EP Patent Application No. 14290010.9 filed Jan. 29, 2014, all of which are incorporated herein by reference.

FIELD OF THE INVENTION

The invention relates to a device for reconstituting a pharmaceutical composition from at least two components.

BACKGROUND OF THE INVENTION

A number of pharmaceutical compositions have a poor stability in an aqueous environment, which may reduce their shelf life to an unacceptable value. This is especially true for large molecules such as biological entities, especially antibody molecules and derived antigen binding molecules, recombinant factors, as well as for some small molecules such as antibiotics and steroid hormones. In some cases, it is possible to extend the shelf life by keeping the liquid composition in a cold environment.

Hence, it may be more advantageous in terms of stability, storage, and ease of shipping to prepare a solid form of the pharmaceutical composition, which may be reconstituted with a solvent shortly before its administration to a patient.

Solid forms of pharmaceutical compositions include powders, freeze-dried (or lyophilized) compositions, spray-dried, spray-freeze dried, vacuum dried or supercritical fluid dried compositions.

Solid forms are to be extemporaneously dissolved using an acceptable solvent composition to produce a solution for injection (so-called "reconstitution").

The reconstitution steps may be carried out manually by the patient, a relative, a nurse or a healthcare professional, depending on the complexity of the reconstitution process.

Although such reconstitution may be straightforward and as short as a few seconds for some specific compositions, it may take up to tens of minutes to reconstitute some pharmaceutical compositions, which is considered as a long time. Long reconstitution times involving complicated series of steps often lead to lower compliance with said protocols, and so finally can result in administration of a wrong dose and even potentially affect the outcome of the treatment.

Another frequent problem is that some compositions are prone to the formation of foam, bubbles, gels or poorly wettable aggregates that require careful reconstitution and are thus considered "hard to reconstitute" per medical standards.

This is particularly the case for pharmaceutical compositions made of high concentrations of large molecules, such as viscous biological drugs such as but not limited to monoclonal antibodies, polyclonal antibodies, certain proteins or polypeptides. It is also the case when the reconstitution is made with less solvent volume than was originally taken out during processing towards a solid form, as it is frequently the case with formulations for injection so as to minimize the volume to be administered.

In any case the most conventional manual process for reconstitution of a solid form typically requires several steps to retrieve the solvent from a first container, inject it in a second container enclosing the solid form of the pharmaceutical composition, apply a given process to obtain a homogenous solution free of foam and/or dry aggregates, withdraw the reconstituted pharmaceutical from the second container for administration.

The reconstitution process requires that the operator pay a specific attention to each step, which is particularly tedious.

Besides, each of these above-mentioned steps themselves may require several object manipulations, including needles or spikes, thus implying a risk of personal injury and/or contamination in the case of a professional treating a patient.

At last, the quality of the reconstituted composition highly depends on the operator: if the steps are not carried out in a proper way, the composition obtained at the end of the reconstitution process may still contain trapped dry lumps or gel zones that can hardly be reached by the solvent and/or trapped air bubbles and/or foam, either in full volume or only limited to a ring at the air/liquid interface.

As a result, all of difficulties or problems abovementioned may result in the drug manufacturers to recommend the training of the user, or have the patient face less than expected medical benefit and/or poor compliance.

BRIEF DESCRIPTION OF THE INVENTION

A goal of the invention is to improve the reproducibility of a reconstitution process and make it little or not dependent from the operator.

Another goal of the invention is to achieve a complete reconstitution of the pharmaceutical composition, even with hard to reconstitute drugs.

The invention provides a device for reconstituting a pharmaceutical composition from at least a first component contained in a first container and a second component contained in a second container, comprising:
  a fluidic unit comprising:
    a first connector configured to mechanically and fluidically couple to the first container,
    a second connector configured to mechanically and fluidically couple to the second container,
    a pump,
    a fluidic circuit comprising channel portions connecting the first connector, the second connector and the pump,
  wherein:
  the second connector comprises an axial port to fluidically couple to the second container when said second container engages the second connector and a radial port in fluidic link with said axial port,
  the first connector comprises:
    a body defining an axial chamber and comprising at least three radial ports connected to the fluidic circuit, and
    a crankpin in rotating engagement within said axial chamber, said crankpin comprising a mounting interface for engaging the first container, a unique axial port intended to fluidically couple to the first container when said first container engages the mounting interface, and a radial port fluidically connected to said axial port, said crankpin comprising at least one channel arranged therein so as to cooperate with the at least three radial ports of the body to selectively connect the axial port of the first connector with at least one channel portion of the fluidic circuit depending on the angular position of the crankpin with respect to the body, a power unit releasably coupled to the fluidic unit and comprising:
a power mechanism for actuating the pump,
transmission means adapted to be connected between an actuator and the crankpin for rotating the first container.

According to an embodiment, the device comprises a base onto which the power unit is mounted, the base comprising an inclination mechanism for selectively tilting the rotation axis of the first container.

According to an embodiment, the second connector comprises a filter within the radial or the axial port of said second connector.

According to an embodiment, the fluidic unit comprises a venting port and the body of the first connector comprises a fourth radial port in fluidic link with said venting port via a channel portion of the fluidic circuit.

The crankpin may comprise a channel adapted to connect the venting port to the pump while the pump is connected to the radial port of the crankpin.

According to an embodiment, the fluidic unit comprises a third connector configured to mechanically and fluidically couple to a third container or an administration means and the body of the first connector comprises a fifth radial port in fluidic link with said crankpin via a channel portion of the fluidic circuit.

The device may comprise a filter between said fifth radial port and the third connector.

According to an embodiment, the axial port of the first connector comprises one spike.

According to an embodiment, the fluidic circuit comprises:
a first channel portion between a first radial port of the body of the first connector and a first port of the pump;
a second channel portion between a second port of the pump and a second radial port of the body of the first connector;
a third channel portion between a third radial port of the body of the first connector and the radial port of the second connector.

According to an embodiment, the pump is a reversible pump.

According to an embodiment, the fluidic unit is made of the assembly of two half-shells, wherein the fluidic circuit is distributed between said half-shells.

Another object of the invention is an assembly for reconstituting a pharmaceutical composition, comprising a reconstitution device as described above, a first container containing a first component coupled to the first connector of said device and a second container containing a second component coupled to the second connector of said device.

According to an embodiment, the first component is a solid form of a pharmaceutical composition and the second component is a solvent.

According to an embodiment, each of the first and second containers is a vial sealed by a septum.

According to an embodiment, in the case the fluidic unit of the reconstitution device comprises a third connector as mentioned above, the assembly comprises a third container or an administration means coupled to the third connector of said reconstitution device.

BRIEF DESCRIPTION OP THE DRAWINGS

Other features and advantages of the invention will be apparent from the detailed description that follows, based on the appended drawings wherein:

FIGS. 3A to 3F illustrate different configurations of the fluid transfer through the fluidic circuit depending on the angular position of the crankpin with respect to the body of the first connector: in FIG. 3B, the crankpin is positioned with respect to the body so as to provide a fluidic link between the radial port of the crankpin fluidically connected to the first container and a venting port, this configuration being intended to equalize the atmospheric pressure and the internal pressure of the first container; in FIG. 3C the crankpin is positioned with respect to the body so as to provide a direct fluidic link between the radial port of the crankpin and the radial port of the second container, this configuration being intended to directly transfer fluid from one container to the other; in FIG. 3E, the crankpin is positioned with respect to the body so as to connect the venting port with a port of the pump through a channel portion while the other port of the pump is connected to the radial port of the crankpin, this configuration being intended to generate pressure within the first container by pumping air from the outside of the device through the venting port and transferring said air to the first container.

DETAILED DESCRIPTION OF EMBODIMENTS OF THE INVENTION

In view of reconstituting a pharmaceutical composition, at least two containers are necessary.

A first container contains a first component (e.g. a solid form of the pharmaceutical composition); a second container contains a second component (e.g. a solvent) to be mixed with the first component in order to obtain the reconstituted pharmaceutical composition. In the description that follows, it is considered that the first component is a solid form of a pharmaceutical composition and the second component is a solvent to be mixed with the solid form in order to convert it into a liquid form, but the invention applies more generally to a reconstitution of a pharmaceutical composition from a first and a second component.

To that end, the solvent is transferred from the second container to the first container and the reconstitution takes place in the first container and/or by a fluidic circulation between both containers.

Depending on the way the pharmaceutical composition is to be administered to a patient, the administration fluid transfer may be carried out by the reconstitution device through an administration means such as a needle, or a link to an infusion set, or a mouthpiece, or a spray nozzle or other suitable means. Alternatively the pharmaceutical composition may be administered with another medical device from the first container which is detached from the device once the pharmaceutical composition is reconstituted or from a another container to which the reconstituted pharmaceutical composition has previously been transferred; said other container may be the second container that initially contained the solvent, or a third container, such as a syringe, a cartridge, a flexible container etc.

Figure 1:
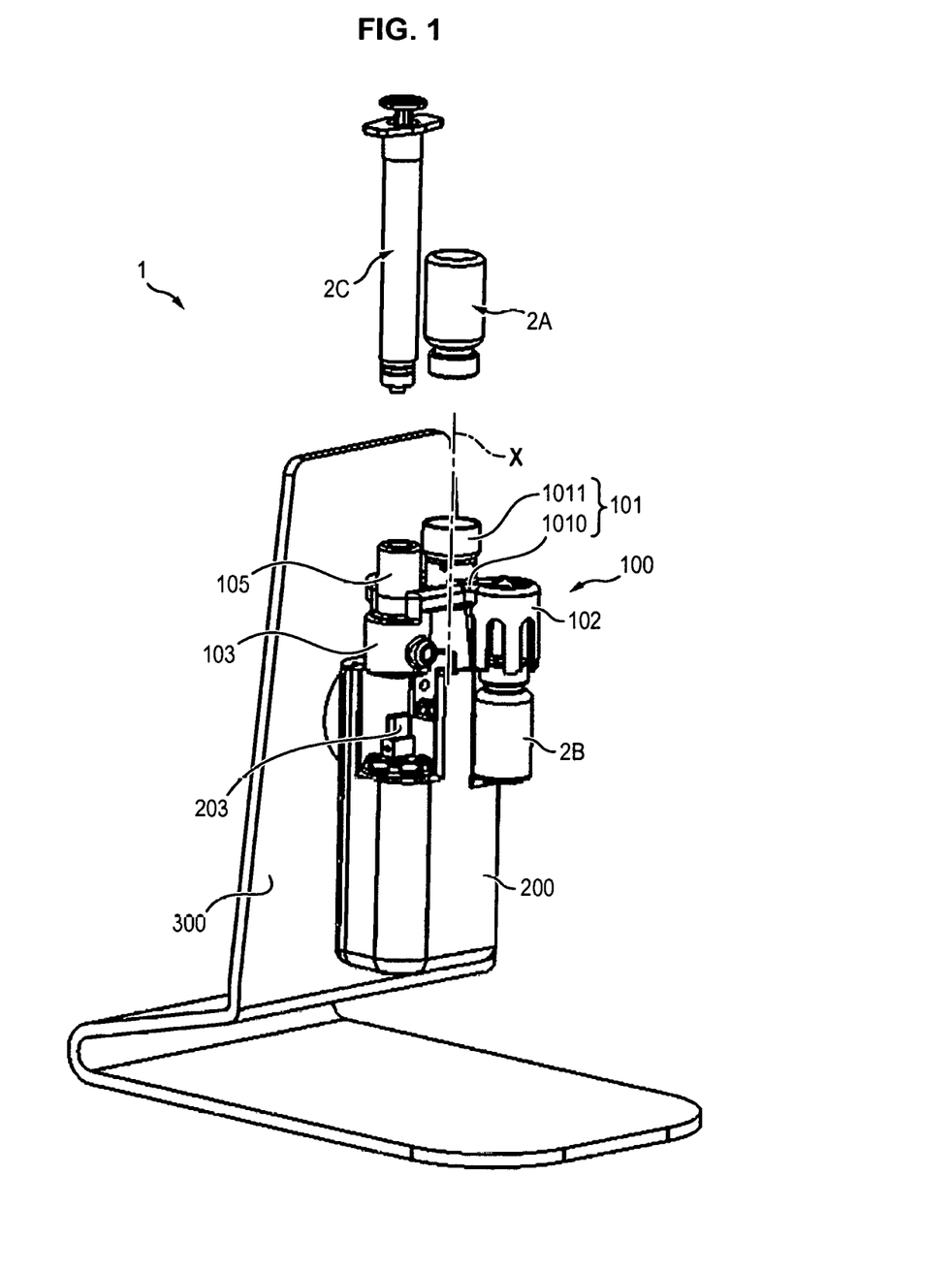
FIG. 1 is an exploded view of a device according to an embodiment of the invention.

FIG. 1 shows an exploded view of a reconstitution device according to an embodiment of the invention.

Said device 1 comprises two main parts that are releasably coupled: a fluidic unit 100 which is intended to receive the first and second containers 2A, 2B (and optionally a third container 2C) in fluidic link through a fluidic circuit and which comprises a pump 103, and a power unit 200 which is intended to actuate the pump 103 in order to provide a fluidic circulation within the fluidic circuit and transmit a rotational movement to a connector 101 coupled to the first container 2A in view of selecting a specific fluidic path within the fluidic circuit and/or providing a mechanical mixing of the content of the first container. The axis of rotation of the first container 2A is referred to as X.

The first container 2A contains the solid form of the pharmaceutical composition and the second container 2B contains the solvent.

In the appended drawings, the device 1 is represented with three containers 2A, 2B, 2C but it shall be understood that the container 2C is optional and that the reconstitution may be implemented with only the first and second containers 2A and 2B.

In the appended drawings, the first and second containers 2A and 2B are represented in the form of a vial, i.e. a bottle-like container that is sealingly closed by a septum, whereas the third container 2C is represented in the form of a syringe. However, it shall be understood that this form of the containers is not limitative and that the invention may be carried out with other container shapes, provided that the connectors of the fluidic unit 100 are adapted accordingly. For example, the second container 2B may be a prefilled syringe, or a cartridge, or a flexible container containing the solvent.

Advantageously, the fluidic unit 100 is disposable, meaning that it is generally used for the reconstitution of one dose of a pharmaceutical composition and that it is subsequently removed from the power unit and disposed of. In view of the reconstitution of a new dose of a pharmaceutical composition, a new fluidic unit is provided in a clean and sterile state and coupled to the power unit 200.

Advantageously, the power unit 200, that is not in contact with the pharmaceutical composition, is durable and reusable, meaning that it is intended to be used over a large amount of time (e.g. several months or years) for reconstituting a plurality of doses of pharmaceutical compositions.

According to a preferred embodiment, the power unit 200 is mounted on a base 300 that comprises an inclination mechanism 301 for selectively tilting the rotation axis X of the first container 2A. As will be described in more detail referring to FIG. 5, this tilting allows creating a mechanical mixing of the pharmaceutical composition and the solvent in the first container 2A and thereby improving the reconstitution and reducing the reconstitution time.

According to an embodiment, the power unit 200 can be removed from the base 300, e.g. when the device is intended for administration of the pharmaceutical composition to the patient via an administration means as mentioned above. In such case, when the power unit is detached from the base, the inclination mechanism may remain attached to the power unit 200 or to the base 300.

The fluidic unit 100 comprises a first connector 101 configured to mechanically and fluidically couple to the first container 2A and a second connector 102 configured to mechanically and fluidically couple to the second container 2B. Optionally, the fluidic unit 100 comprises a third connector 105 configured to mechanically and fluidically couple to the third container 2C or to an administration means as mentioned above (not shown).

By "mechanical and fluidic coupling" is meant that each connector is adapted (i) to be secured in a releasable way to the respective container in order to support it during the reconstitution process via a suitable mounting interface, and (ii) to provide a fluidic link between the inside of the respective container and a fluidic circuit 104 of the fluidic unit 100 that will be described in more detail below. The skilled person is capable of designing the connectors to fulfill both functions depending on the containers and/or an administration means that are to be connected thereto.

The fluidic unit 100 further comprises a pump 103 that is intended, when actuated, to generate a circulation of fluid in the fluidic circuit 104 between the containers.

Advantageously, the pump 103 is a volumetric pump, so as to master the volumes of the transfers between the suction and the discharge ends, thereby mastering the volumes being transferred between the containers as well as impose pressure or vacuum. Advantageously, the pump 103 is a blocking pump, so as to seal channel portions of the fluidic circuit from each other when not actuated.

According to a preferred embodiment, the pump 103 is a reversible pump.

However, the skilled person could use a non-reversible pump without departing from the scope of the present invention. In such case, the skilled person would only have to adapt the design of the channels of the crankpin of the first connector and of the fluidic circuit 104 so as to allow all the necessary channel connections.

The power unit 200 comprises a power mechanism 203 for actuating the pump 103.

The power unit 200 further comprises coupling means (not shown) that is intended to be coupled between an actuator (not shown) and the crankpin 1011 for rotating the crankpin of the first connector 101 and thus the first container 2A that is connected thereto. According to an embodiment, the actuator may be included in the power unit 200. According to another embodiment, the actuator is included in the base 300 and connected to the coupling means for transmitting movement of the actuator to the crankpin.

The rotation of the crankpin can be carried out stepwise (especially in view of setting the crankpin 1011 in a specific position with respect to the fluidic circuit 104), or continuously over a given time period (especially in view of mixing the content of the first container 2A at a determined rate).

The coupling of the fluidic unit 100 to the power unit 200 and/or actuator(s) of base 300 can be carried out by any suitable means, such as mechanical means, or magnetic means. This coupling is releasable, thereby allowing disposing of the fluidic unit 100 and reusing the power unit 200 and optionally releasing the motor unit from base 300 for a portion of the operation of the sequence.

The actuation of the pump 103 and the rotation of the crankpin 1011 can be controlled by an operator or may be fully automatized. To that end, a control system (not shown) operates according to a specific algorithm in order to actuate the pump and the crankpin according to a determined sequence.

Figure 2A:
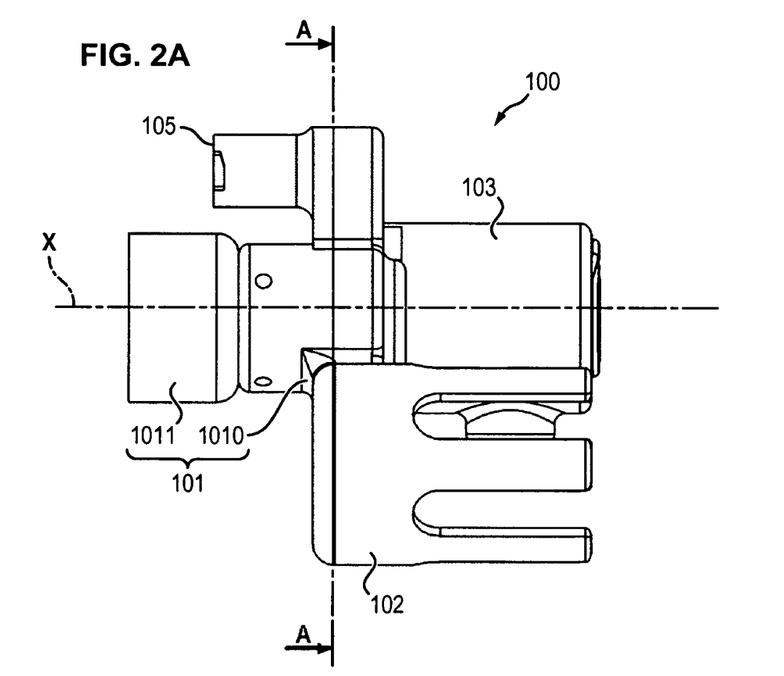
FIG. 2A is a side view of the fluidic unit.

FIG. 2A shows a side view of the fluidic unit 100.

Figure 2B:
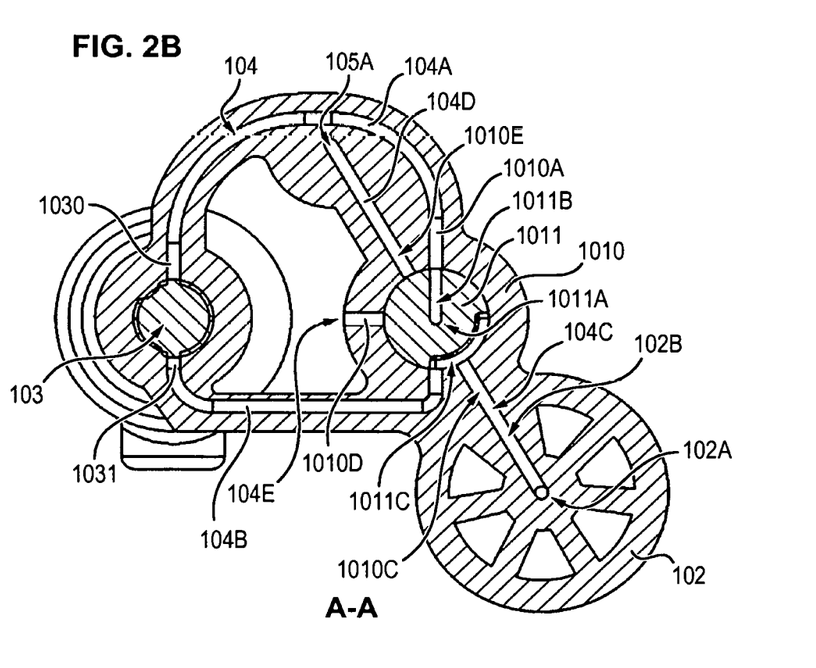
FIG. 2B is a sectional view of the fluidic unit at the level of the fluidic circuit.

FIG. 2B is a sectional view of the fluidic unit 100 at the level of the fluidic circuit 104.

The fluidic circuit 104 comprises channel portions connecting the first connector 101, the second connector 102 and the pump 103. When the fluidic unit comprises a third connector 105 for a third container 2C or an administration means, the fluidic circuit 104 also comprises at least one channel portion to connect the third connector to the rest of the fluidic circuit.

The first connector 101 comprises a body 1010 defining an axial chamber and comprising at least three radial ports 1010A, 1010B, 1010C connected to channel portions 104A, 104B, 104C of the fluidic circuit 104. The axial direction is perpendicular to the plane of FIG. 2B.

A crankpin 1011 is in rotating engagement according to axis X within the axial chamber of the body 1010.

The crankpin 1011 comprises a mounting interface for engaging the first container 2A.

The crankpin 1011 comprises one axial port 1011A intended to fluidically couple to the first container 2A when said container engages the mounting interface. For example, if the first container 2A is a vial sealed by a septum, said unique axial port 1011A may consist of a spike or a needle for piercing the septum. Said axial port 1011A is unique, meaning that there is only one fluidic path between the first container 2A and the fluidic circuit 104.

The crankpin 1011 comprises a radial port 1011B that is fluidically connected to the axial port 1011A.

Besides, the crankpin 1011 comprises at least one channel 1011C arranged therein so as to selectively cooperate with the radial ports 1010A, 1010B, 1010C of the body, and thus to the channel portions of the fluidic circuit 104. For example, said at least one channel may consist of a groove created in the crankpin wall, the position and dimension of said grooves being determined so as to provide the desired connections. The skilled person is able to design the crankpin depending on the arrangement of the channels of the fluidic circuit 104. The channels may be arranged to provide simultaneous fluidic connections, such as between radial port 1010E and channel portion 104A on the one hand and at the same time between radial port 1011B and channel portion 104B (see 7n FIG. 3D).

The body 1010 of the first connector is sealed with respect to the crankpin 1011. For example, a seal (not shown) is arranged on the crankpin or on the body.

The second connector 102 comprises an axial port 102A to fluidically couple to the second container 2B when said second container engages the second connector and a radial port 102B in fluidic link with said axial port 102A. For example, if the second container 2B is a vial sealed by a septum, said axial port 102A may consist of a spike or a needle for piercing the septum.

The second connector 102 may comprise a filter (not shown) arranged within the radial port 102B or the axial port 102A. Such a filter may be advantageous in case the reconstituted pharmaceutical composition is transferred from the first container 2A to the second container 2B. Indeed, the filter may thus retain certain molecules from the pharmaceutical composition.

In the embodiment shown in FIG. 2B, the fluidic unit 104 comprises the following channel portions:
a channel portion 104A extending between the first radial port 1010A of the body of the first connector 101 and the first radial port 1030 of the pump;
a channel portion 104B extending between the second radial port 1031 of the pump 103 and the second radial port 1010B of the body of the first connector 101;
a channel portion 104C extending between the third radial port 1010C of the body of the first connector 101 and the radial port 102B of the second connector 102.

Optionally, if the device comprises a third connector 105, the fluidic circuit may comprise a fourth radial port 104D extending between the radial port 105B of said third connector 105 and an additional radial port 1010E of the body of the first connector 101. The fluidic unit may comprise a filter (not shown) between the radial port 1010E and the radial port 104D. Indeed, the filter may thus retain certain molecules from the pharmaceutical composition.

Optionally, the body of the first connector 101 may comprise a venting port 104E which is open to the atmosphere surrounding the device. In such case, the body of the first connector 101 comprises a port 1010D in fluidic link with said venting port 104E.

Preferably, the venting port 104E includes a filter (not shown) in order to prevent contaminants from entering into the fluidic circuit. Such a filter is classically used in the pharmaceutical industry.

Figure 6:
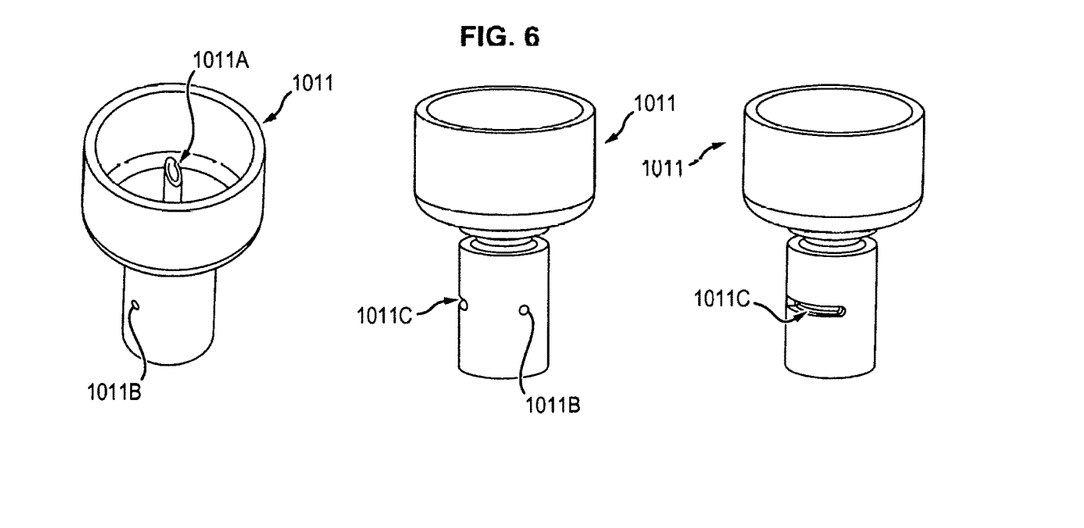
FIG. 6 shows three perspective views of an embodiment of the crankpin.

FIG. 6 shows three perspective views of a crankpin according to an embodiment of the invention. As can be seen in view A, the axial port 1011A of the crankpin consists of one spike or needle. The crankpin 1011 further comprises a radial port 1011B that is in fluidic link with the axial port 1011A and a peripheral groove 1011C that forms a channel adapted to connect different portions of the fluidic unit. Said peripheral groove 1011C is arranged within the wall of the crankpin 1011 and is not in fluidic link with axial and radial ports 1011A, 1011B FIGS. 3A to 3F show different configurations of the fluid transfer through the fluidic circuit 104 depending on the angular position of the crankpin 1011 with respect to the body 1010 of the first connector. The arrows show the direction of the fluid flow.

Figure 3A:
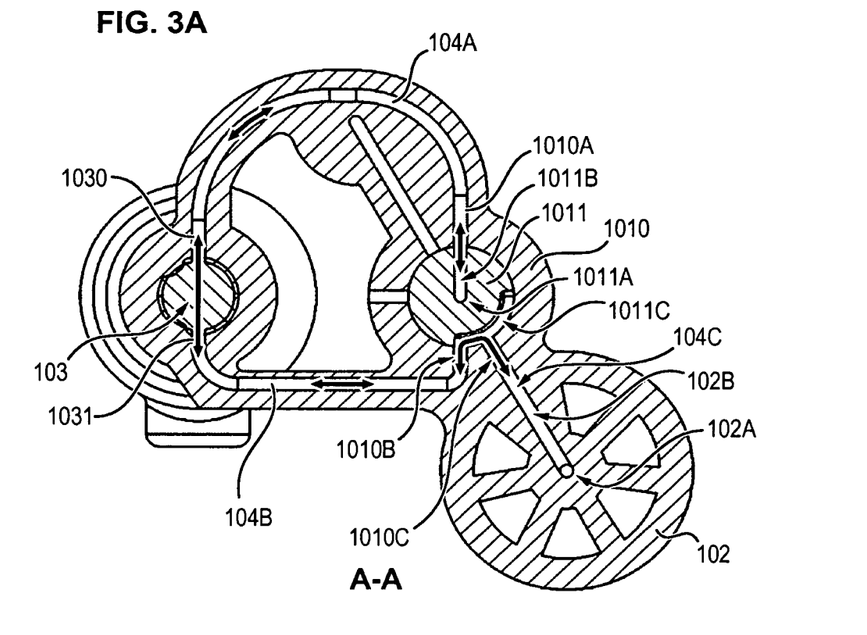
in FIG. 3A, the crankpin is positioned with respect to the body so as to provide a fluidic link between the radial port of the crankpin and the pump on the one hand, and between the pump and the radial port of the second connector on the other hand, this configuration being intended to transfer fluid from the first container to the second container or vice versa.

In FIG. 3A, the crankpin 1011 is positioned with respect to the body 1010 so as to provide a fluidic link between the radial port 1011B of the crankpin and the first port 1030 of the pump 103 on the one hand (via channel portion 104A), and between the second port 1031 of the pump 103 and the radial port 102B of the second connector 102 on the other hand (successively via channel portion 104B, radial port 1010B, peripheral channel 1011C of the crankpin 1011 and radial port 1010C).

Such a position may typically be used in view of transferring the solvent from the second container 2B to the first container 2A containing the solid form of the pharmaceutical composition.

Conversely, said position of the crankpin may be used to transfer the reconstituted pharmaceutical composition from the first container 2A to the second container 2B.

Figure 3B:
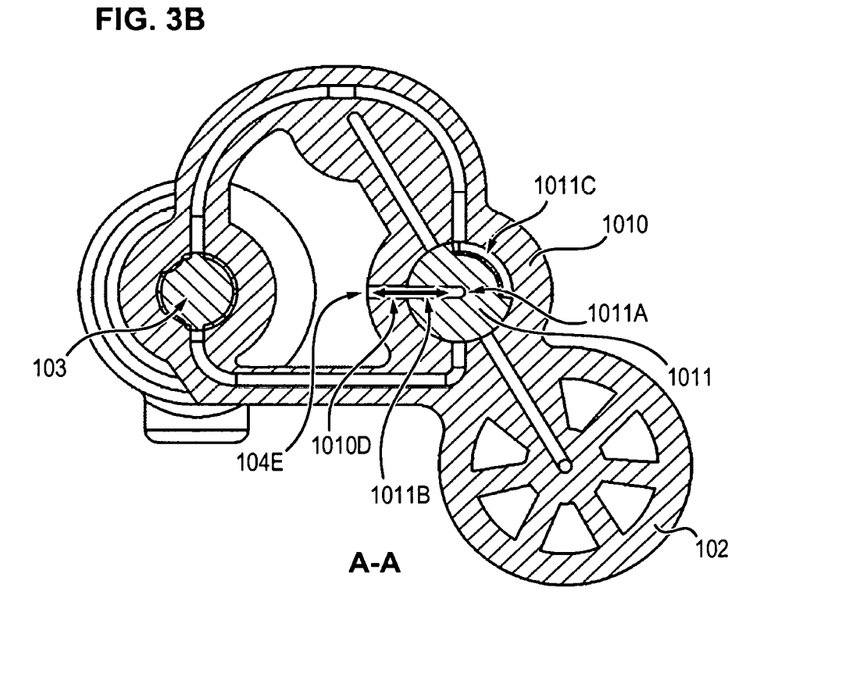

In FIG. 3B, the crankpin 1011 is positioned with respect to the body 1010 so as to provide a fluidic link between the radial port 1011B of the crankpin fluidically connected to the first container 2A and venting port 104E (via radial port 1010D). In such case, the peripheral channel 1011C of the crankpin does not establish any fluidic connection between different parts of the fluidic unit.

This crankpin position may typically be used in view of equalizing the atmospheric pressure and the internal pressure of the first container 2A.

For example, if the first container 2A is under vacuum or over pressure, this position of the crankpin 1011 allows the content of the first container to return to atmospheric pressure.

Figure 3C:
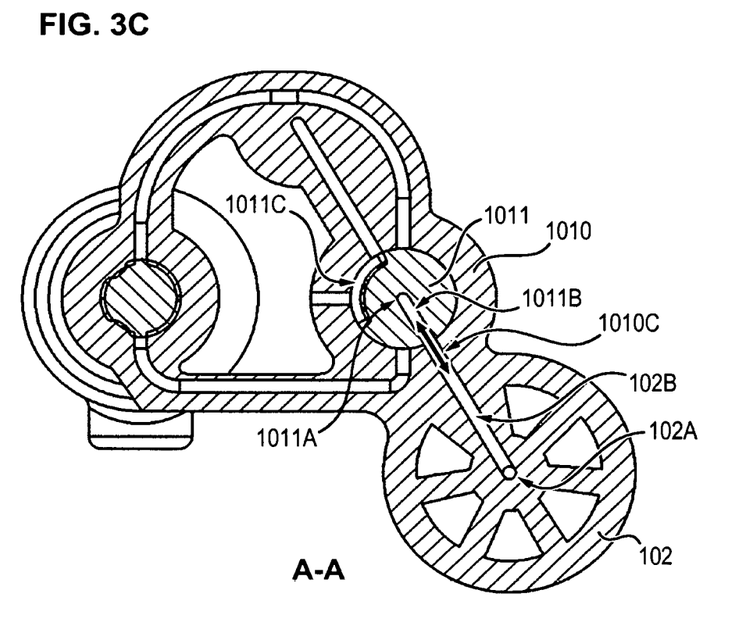
Figure 3D:
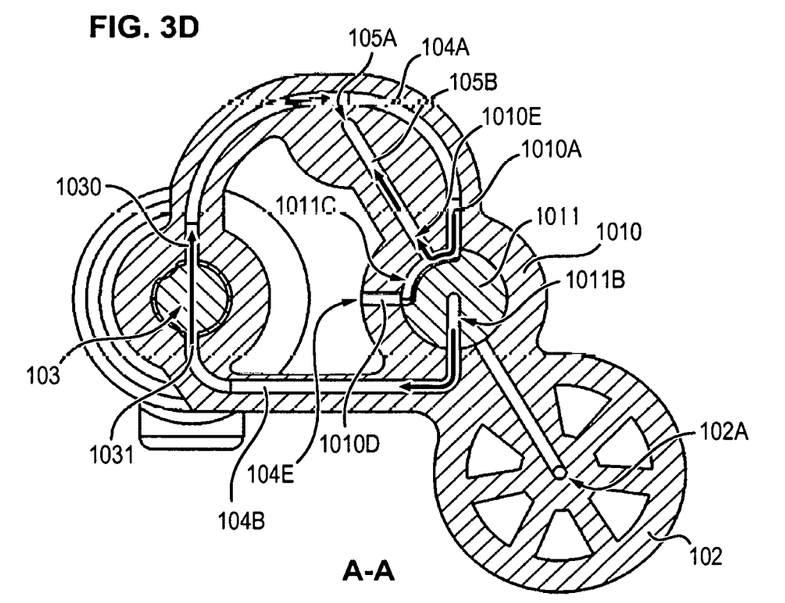
in FIG. 3D the crankpin is positioned with respect to the body so as to provide a fluidic link between the radial port of the crankpin and the pump on the one hand, and between the pump and a port of a third connector on the other hand, this configuration being intended for example to transfer fluid from the first container to a third container for administration of the reconstituted composition to a patient.
Figure 3E:
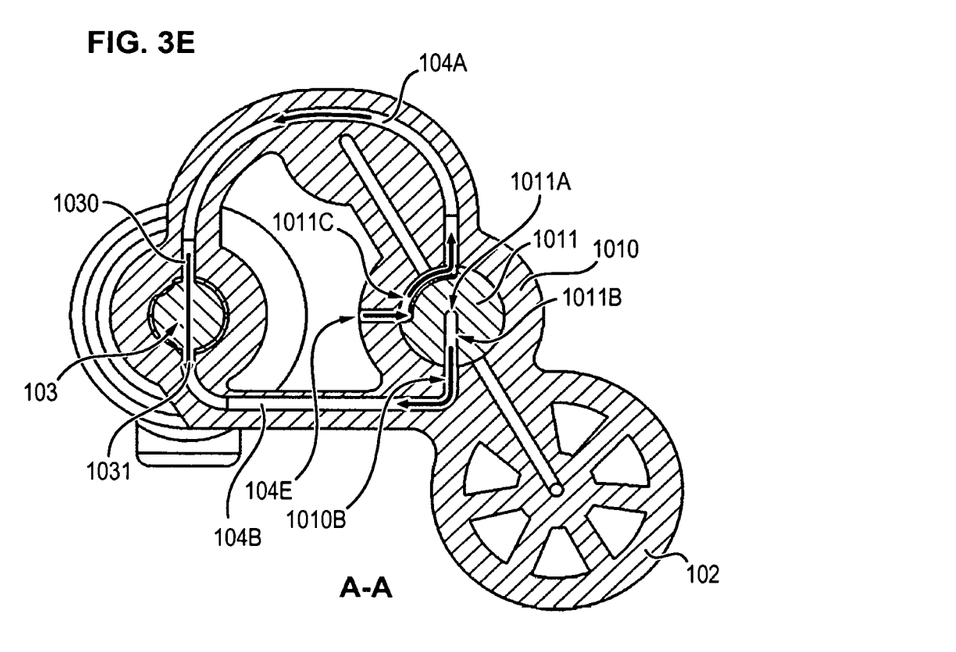

According to an alternative embodiment illustrated in FIG. 3E, the crankpin 1011 comprises a channel 1011C connecting the radial port 1010D and the radial port 1010A while the radial port 1010B is connected to channel portion 104B. In this way, the pump 103 may be used to generate pressure within the first container 2A, by pumping air from the outside of the device through the venting port 104E and transferring said air to the first container 2A. In such case, the first container 2A is in the position illustrated in FIG. 1, i.e. the septum is oriented toward the bottom.

If the first container 2A is in the opposite position as the position illustrated in FIG. 1, i.e. the septum is oriented toward the top, such arrangement of the crankpin may also be used either to draw vacuum in the first container 2A or to create an overpressure in the first container 2A, depending on the direction of actuation of the pump 103. The skilled person would be able to arrange the crankpin design to permit such overpressure and/or vacuum generations in any container connected to the reconstitution device.

In FIG. 3C the crankpin 1011 is positioned with respect to the body 1010 so as to provide a direct fluidic link between the radial port 1011B of the crankpin and the radial port 102B of the second connector 102.

This crankpin position allows directly transferring fluid from one container to the other as a result of the difference of pressure between them.

In FIG. 3D the crankpin 1011 is positioned with respect to the body 1010 so as to provide a fluidic link between the radial port 1011B of the crankpin and the port 1031 of the pump 103 (via channel portion 104B) on the one hand, and between the pump 103 and the radial port 105B of a third connector (via channel portion 104A, radial port 1010A, channel 1011C of the crankpin 1011, radial port 1010E and channel portion 104D) on the other hand.

This crankpin position may be used in view of transferring fluid from the first container 2A to the third container 2C or to an administration means thanks to the pump 103.

In the specific configuration illustrated in FIG. 3D, since the peripheral channel 1011C of the crankpin fluidically connects the venting port 104E to the pump 103, a hydrophobic filter (not shown) is arranged within the venting port 104E so as to allow air exiting from the fluidic unit while preventing liquid from exiting from the fluidic unit.

According to an embodiment, only a specific dose of the reconstituted pharmaceutical composition can be transferred from the first container 2A to the third container 2C and later be administered to a patient.

Alternatively, the whole content of the first container 2A may be transferred to the third container 2C.

According to another embodiment, there is no container connected to the third connector 105 but or another means of administration such as—but not limited to—a needle, or a link to an infusion set, or a mouthpiece, or a spray nozzle, this means being used to administer directly or indirectly the reconstituted pharmaceutical composition to the patient from the first container 2A via the fluidic circuit 104.

According to an embodiment, only a specific dose of the reconstituted pharmaceutical composition can be directly administered to a patient via the pump 103 though appropriate means of administration, such as—but not limited to—a needle, or a link to an infusion set, or a mouthpiece, or a spray nozzle.

Figure 3F:
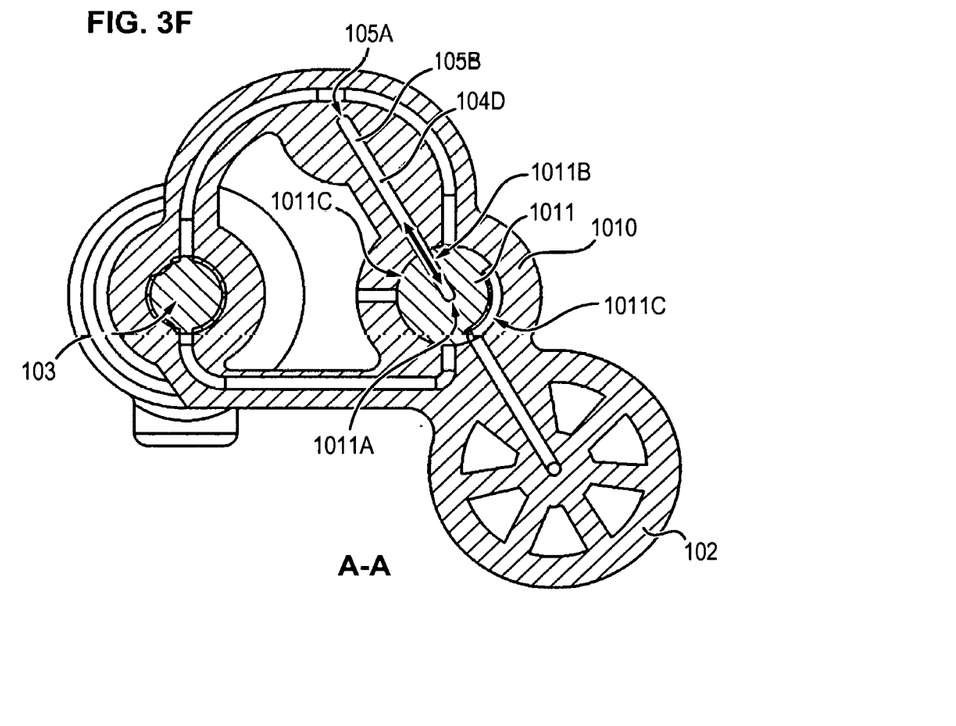
in FIG. 3F the crankpin is positioned with respect to the body so as to provide a direct fluidic link between the radial port of the crankpin and the radial port of the third connector, this configuration being intended for example to transfer fluid between first and third containers as a result of the difference of pressure between them.

In FIG. 3F the crankpin 1011 is positioned with respect to the body 1010 so as to provide a direct fluidic link between the radial port 1011B of the crankpin and the radial port 105B of the third connector 105.

This crankpin position allows directly transferring fluid from one container to the other as a result of the difference of pressure between them.

If it is intended to transfer fluid (e.g. a solvent) from the third container 2C to the first container 2A, the respective positions of both containers should be opposite to the positions shown in FIG. 1. To that end, the inclination mechanism 301 may be actuated to rotate the power unit and the fluidic unit by an angle of 180° from the configuration of FIG. 1.

Figure 4:
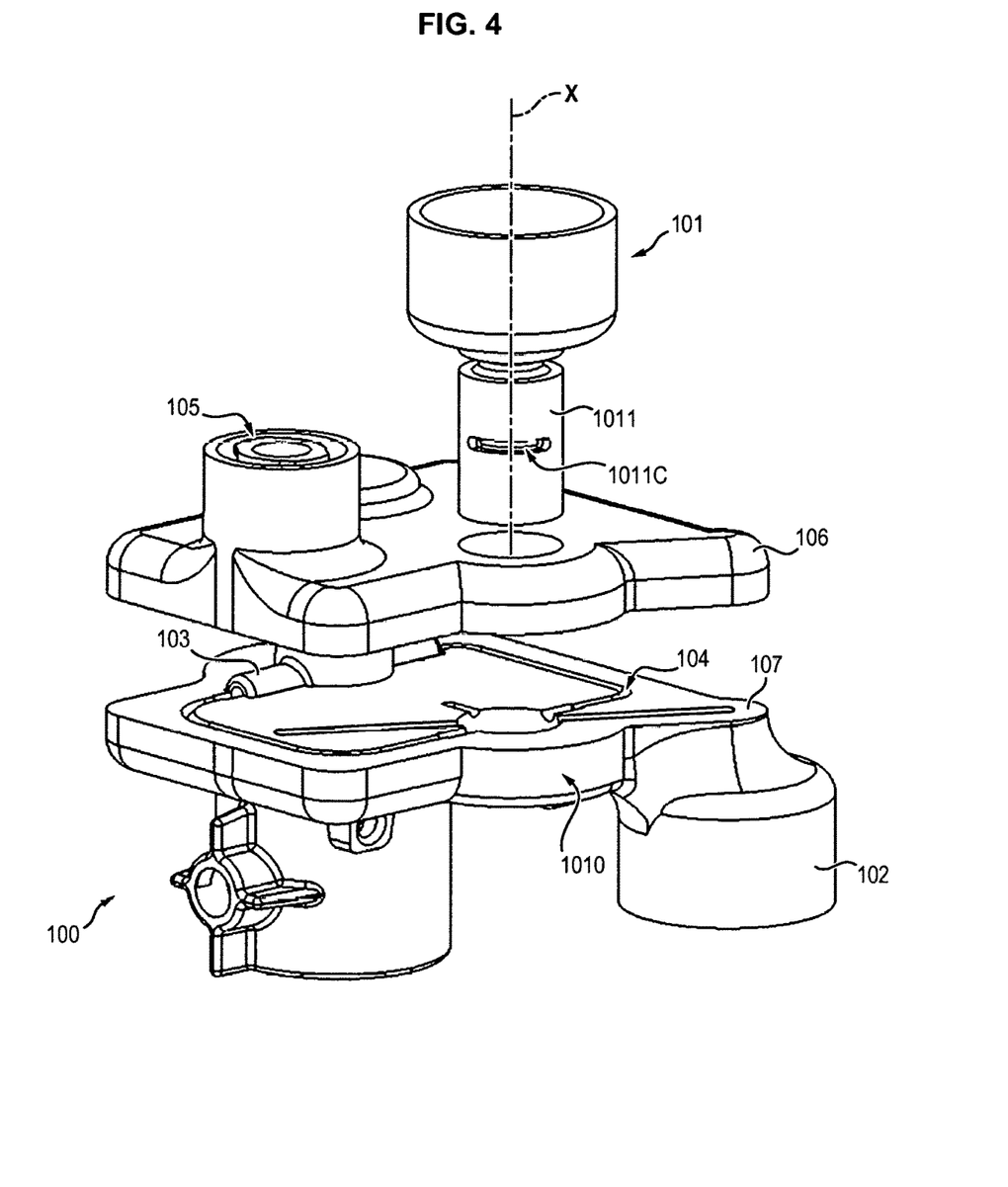
FIG. 4 illustrates an embodiment of the fluidic part wherein said fluidic part is made of the assembly of two half-shells.

FIG. 4 shows an embodiment of the fluidic unit wherein said fluidic unit 100 is made of the assembly of two half-shells 106, 107.

For example, the half-shells may be made by plastic molding and secured together by laser welding, ultrasonic welding, solvent assembly, gluing, screws or by any other suitable means.

A seal (not shown) may be arranged between the two half-shells 106, 107, or the assembly mean itself may provide the sealing of the fluidic circuit.

The junction between said half-shells may take place along a plane that is parallel to at least one part of the fluidic circuit 104.

For example, the plane corresponds to a plane of symmetry of channel portions.

Hence, each half-shell comprises a part of the fluidic circuit.

Besides, the body of the first connector, the second connector and, if any, the third connector, may be made integral with one of the half-shells.

Figure 5:
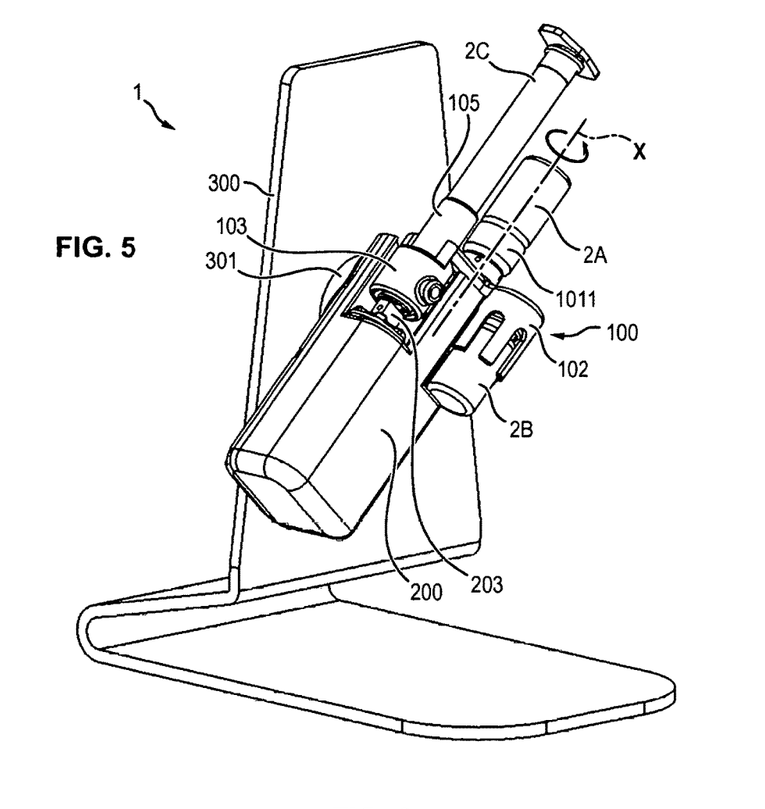
FIG. 5 is a view of the device in an assembled state, the rotation axis of the first container being tilted with respect to the gravitational axis so as to provide a mechanical mixing of the content of the first container.

FIG. 5 is a view of the reconstitution device 1 in an assembled state, wherein the rotation axis X of the first container 2A is tilted with respect to the gravitational axis so as to provide a mechanical mixing of the content of the first container.

For example, the angle may be of between 20° and 90°, preferably about 45°. In such case, the angle between the rotation axis of the container 2A and the gravitational axis makes for a low shear mixing of the content of the container and for the leaching of the wet solution on the dry adherences of solid forms on the container wall, thus recovering more dry form, and consequently improving overall recovery.

A reconstitution device as described above can be used for automatic reconstitution—and, in some cases, administration—of a pharmaceutical composition.

In particular, the reconstitution device allows managing the pressure within the container comprising the mixture of the pharmaceutical composition and the solvent according to various time frames.

In the examples of reconstitution processes that are described below, it is supposed that the first container contains a solid form of a pharmaceutical composition and that the second container contains a solvent.

Figure 7A:
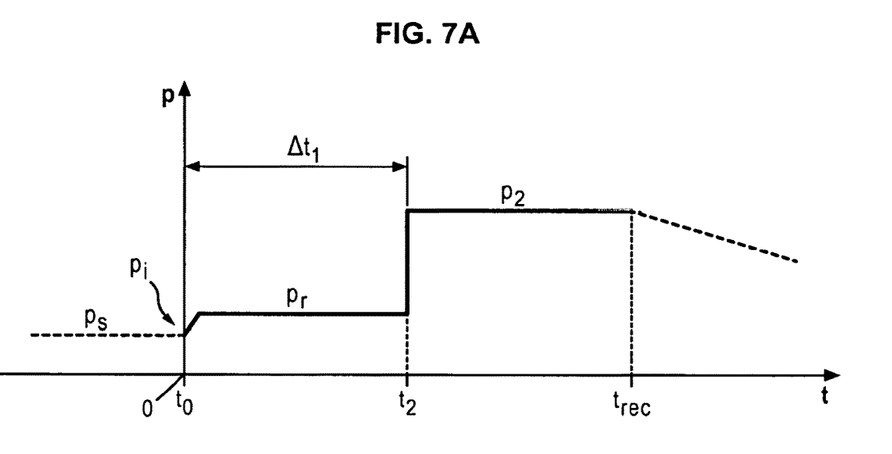
FIGS. 7A to 7D show different possible time frames of a reconstitution process carried out using a reconstitution device according to the invention.

FIG. 7A illustrates an example of time frame for an embodiment of a reconstitution process that can be performed by a device according to the invention.

The reconstitution process is considered to begin at time $t_0$, which corresponds to the start of introduction of the solvent from the second container to the first container.

Just before introduction of the solvent, the pressure within the first container is the initial pressure $p_i$.

Said pressure may be the pressure within the first container during its previous storage, referred to as storage pressure ($p_s$).

Figure 7B:
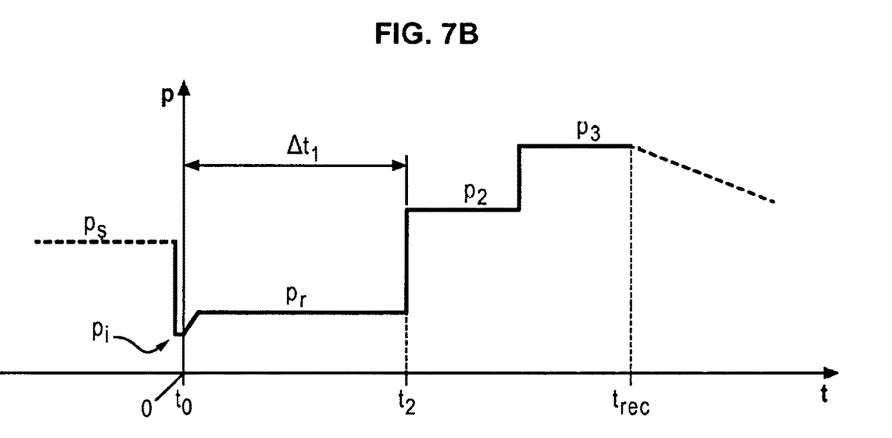

Alternatively, as illustrated in FIG. 7B, the pressure within the first container during storage may be a pressure $p_s$ different (either greater or smaller) to $p_i$, and the pressure is set to $p_i$ a short time before beginning of the reconstitution process.

In view of introducing the solvent in the first container, the crankpin of the first connector is set to a position as shown in FIG. 3A or FIG. 3C. If the first container is not under vacuum, or the difference of pressure between the first and second containers is not sufficient, or in order to master the doses being transferred, the transfer of the solvent contained in the second container is assisted by the pump 103 (FIG. 3A); if the first container is under vacuum, or the difference of pressure between the two containers is sufficient and the resulting pressure may not be controlled, the solvent may be transferred directly from the second container due to the difference of pressure between both containers (FIG. 3C). The crankpin 1011 may be moved to another position immediately after the appropriate solvent volume has been added to the first container initially containing the solid form of pharmaceutical composition, in order not to introduce additional air that may render further reconstitution process more difficult.

The introduction of the solvent in the first container has the effect of slightly modifying the pressure; the resulting pressure is thus referred to as $p_r$.

This resulting pressure does not require to be quantified precisely; however, the resulting pressure $p_r$ is advantageously maintained during a defined time $\Delta t_1$.

At a defined time $t_2$ that corresponds to $t_0 + \Delta t_1$, which is a time when the reconstitution is not yet complete, the pressure within the first container is increased to a pressure $p_2$ that is greater than $p_i$ and $p_r$.

In the case the pressure $p_r$ within the first container is below atmospheric pressure, said increase may consist in releasing vacuum from the first container. This can be done by setting the crankpin of the first connector to a position as shown in FIG. 3B, so as to create a fluidic link between the air surrounding the reconstitution device and the inside of the first container and thus set the pressure within the first container to atmospheric pressure. Alternatively, in the case the pressure $p_r$ within the first container is above atmospheric pressure, the pressure within the first container may be further increased by making use of the pump 103: in such case, the crankpin 1011 is set to a position as shown in FIG. 3E.

In order to promote reconstitution of the pharmaceutical composition, the first container 2A is rotated during at least a part of the reconstitution process. To that end, the crankpin 1011 is rotated at a given rate and during a given time while the rotation axis of the first container is tilted with respect to the gravitational direction by the inclination mechanism 301, as shown in FIG. 5. In this way, a mechanical mixing of the mixture of the pharmaceutical composition and the solvent is obtained. Alternatively, the fluidic unit 100 or the power unit 200 may be held by a user in the desired tilted orientation during mechanical mixing.

In a particular embodiment, such a mixing step may be carried out after introducing the solvent in the first container, before increasing the pressure to $p_2$ within the first container. Alternatively, the mixing step may be carried out after the pressure within the first container has been increased to $p_2$. In yet another particular embodiment the mixing step may be performed before and after increasing the pressure to $p_2$.

The pressure within the first container is maintained at pressure $p_2$ until complete reconstitution is observed (time $t_{rec}$). After time $t_{rec}$, the reconstituted composition may be retrieved from the first container and either transferred to the second container (to that end, the crankpin of the first connector is set to a position as shown in FIG. 3A), to a third container (to that end, the crankpin is set to a position as shown in FIG. 3D) or to an administration means (to that end, the crankpin is set to a position as shown in FIG. 3D).

FIG. 7B illustrates an example of a time frame for a reconstitution process according to another embodiment of the invention.

As compared to the process of FIG. 7A, the process of FIG. 7B comprises an additional step of further increasing the pressure within the first container to a pressure $p_3$, after a defined time at $p_2$ and before complete reconstitution of the pharmaceutical composition is observed. Said increased pressure $p_3$ within the first container can be obtained by setting the crankpin in the position shown in FIG. 3E and by actuating the pump.

Figure 7C:
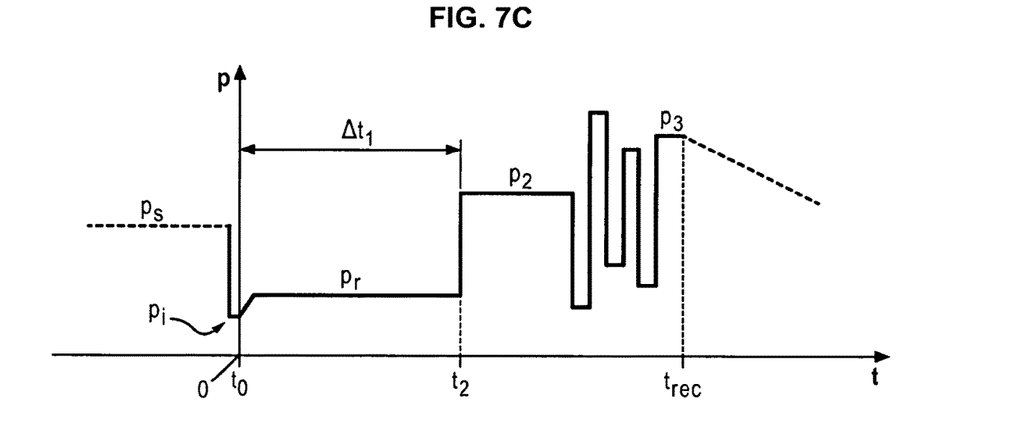

FIG. 7C illustrates an example of a time frame for a reconstitution process that comprises, after applying pressure $p_2$ and before applying pressure $p_3$, pressure cycles comprising successive pressure increases and decreases. Said pressure cycles can be obtained while the crankpin is in the position of FIG. 3E and by actuating the pump alternately in both directions.

Figure 7D:
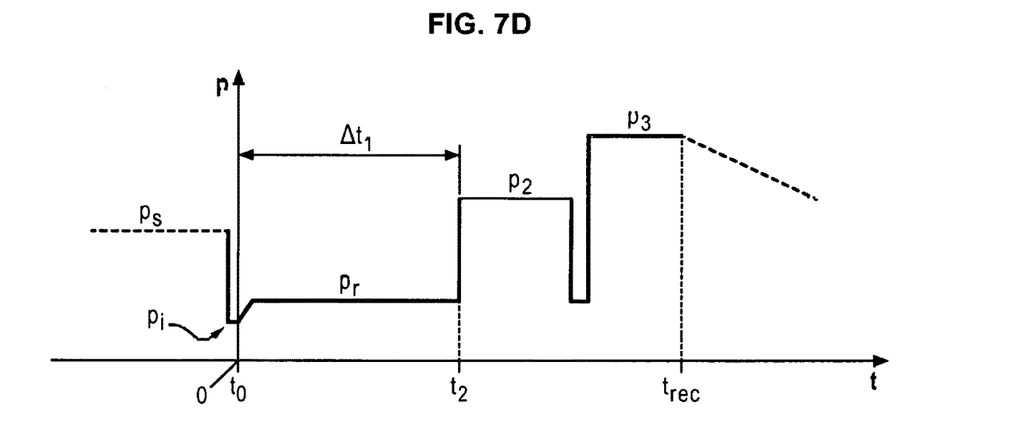

FIG. 7D illustrates a variation of the time frame shown in FIG. 7C comprising only one pressure decrease from pressure $p_2$ followed by a pressure increase to pressure $p_3$.

One advantage of such reconstitution processes is that, contrary to reconstitution processes known in the art, little or no crown of bubbles remain at the surface of the pharmaceutical composition following reconstitution. Such bubble and/or foam reduction results in increased recovery of useable composition from the container, thus requiring lower starting amounts of the solid form pharmaceutical composition in the container at production for a given retrieval/dose objective.

Once the pharmaceutical composition is reconstituted, it may be administered to the patient via the fluidic unit 100. For example, the fluidic unit 100 may comprise a third connector 105 coupled to an administration means, such as an infusion set. When the reconstitution is completed, the power unit 200 and the fluidic unit 100 are together removed from the base 300 as a portable device and carried by the patient during infusion of the pharmaceutical composition, the pump 103 of the fluidic unit 100 being actuated by the power mechanism 203. Once infusion is completed, the fluidic unit 100 may be removed from the power unit 200 and disposed of, whereas the power unit 200 as well as the base 300 may be later used for reconstitution of another dose of a pharmaceutical composition.

The invention claimed is:

1. A device for reconstituting a pharmaceutical composition from at least a first component contained in a first container and a second component contained in a second container, comprising:
   a fluidic unit; and
   a power unit releasably coupled to the fluidic unit,
   wherein the fluidic unit comprises:
      a first connector comprising a body defining an axial chamber and a rotatable crankpin arranged in the axial chamber, the crankpin comprising a mounting interface configured to mechanically couple to the first container, the crankpin further comprising an axial port configured to fluidically couple to the first container when said first container engages the mounting interface, and a radial port fluidically connected to the axial port of the first connector;
      a second connector configured to mechanically and fluidically couple to the second container, the second connector comprising an axial port to fluidically couple to the second container when said second container engages the second connector and a radial port in fluidic link with the axial port of the second connector;
      a pump; and
      a fluidic circuit comprising channel portions connecting the first connector, the second connector and the pump;
   wherein the body of the first connector comprises at least three radial ports connected to the fluidic circuit,
   wherein the crankpin comprises at least one channel configured to cooperate with the at least three radial ports of the body of the first connector to selectively connect the axial port of the first connector with at least one channel portion of the fluidic circuit depending on the angular position of the crankpin with respect to the body, and
   wherein the power unit comprises:
      a power mechanism for actuating the pump; and
      transmission means adapted to be connected between an actuator and the crankpin for rotating the first container.

2. The device according to claim 1, comprising a base onto which the power unit is mounted, the base comprising an inclination mechanism for selectively tilting the rotation axis of the first container.

3. The device according to claim 1, wherein the second connector comprises a filter within the radial or the axial port of said second connector.

4. The device according to claim 1, wherein the fluidic unit comprises a venting port and the body of the first connector comprises a fourth radial port in fluidic link with said venting port via a channel portion of the fluidic circuit.

5. The device according to claim 4, wherein the crankpin comprises a channel adapted to connect the venting port to the pump while the pump is connected to the radial port of the crankpin.

6. The device according to claim 1, wherein the fluidic unit comprises a third connector configured to mechanically and fluidically couple to a third container or an administration means and wherein the body of the first connector comprises a fifth radial port in fluidic link with said crankpin via a channel portion of the fluidic circuit.

7. The device according to claim 6, further comprising a filter between said fifth radial port and the third connector.

8. The device according to claim 1, wherein the axial port of the first connector comprises one spike.

9. The device according to claim 1, wherein the fluidic circuit comprises:
   a first channel portion between a first radial port of the body of the first connector and a first port of the pump;
   a second channel portion between a second port of the pump and a second radial port of the body of the first connector;
   a third channel portion between a third radial port of the body of the first connector and the radial port of the second connector.

10. The device according to claim 1, wherein the pump is a reversible pump.

11. The device according to claim 1, wherein the fluidic unit is made of the assembly of two half-shells, wherein the fluidic circuit is distributed between said half-shells.

12. An assembly for reconstituting a pharmaceutical composition, comprising a reconstitution device according to claim 1, a first container containing a first component coupled to the first connector of said device and a second container containing a second component coupled to the second connector of said device.

13. The assembly according to claim 12, wherein the first component is a solid form of a pharmaceutical composition and the second component is a solvent.

14. The assembly according to claim 12, wherein each of the first and second containers is a vial sealed by a septum.

15. The assembly according to claim 12, wherein the fluidic unit comprises a third connector configured to mechanically and fluidically couple to a third container or an administration means and wherein the body of the first connector comprises a fifth radial port in fluidic link with said crankpin via a channel portion of the fluidic circuit, the assembly further comprising a third container or an administration means coupled to the third connector of said reconstitution device.

* * * * *